US012673212B2

(12) United States Patent
Wasserman et al.

(10) Patent No.: US 12,673,212 B2
(45) Date of Patent: Jul. 7, 2026

(54) PYROELECTRIC-BASED TEMPERATURE SENSING OF TRANSDUCER ARRAYS FOR APPLYING TUMOR TREATING FIELDS (TTFIELDS)

(71) Applicant: Novocure GmbH, Root (CH)

(72) Inventors: Yoram Wasserman, Haifa (IL); Stas Obuchovsky, Haifa (IL); Nataliya Kuplennik, Haifa (IL)

(73) Assignee: Novocure GmbH, Baar (CH)

( * ) Notice: Subject to any disclaimer, the term of this patent is extended or adjusted under 35 U.S.C. 154(b) by 1155 days.

(21) Appl. No.: 17/550,049

(22) Filed: Dec. 14, 2021

(65) Prior Publication Data

US 2022/0193435 A1    Jun. 23, 2022

Related U.S. Application Data

(60) Provisional application No. 63/126,911, filed on Dec. 17, 2020.

(51) Int. Cl.
*A61N 1/40* (2006.01)
*H10N 15/10* (2023.01)

(52) U.S. Cl.
CPC .............. *A61N 1/40* (2013.01); *H10N 15/10* (2023.02)

(58) Field of Classification Search
CPC .... A61N 1/0404; A61N 1/40; A61N 1/36002; A61N 1/0476; A61N 1/32; A61N 1/0492; A61N 1/0408; A61N 1/3603
(Continued)

(56) References Cited

U.S. PATENT DOCUMENTS 5,193,911 A * 3/1993 Nix ......................... H10N 15/10
                                                                       438/54
6,868,289 B2 * 3/2005 Palti ......................... A61N 1/40
                                                                       607/76
(Continued)

FOREIGN PATENT DOCUMENTS

CN        109260596 A      1/2019

OTHER PUBLICATIONS

International Search Report and Written Opinion issued in application No. PCT/IB2021/061665 dated Jul. 22, 2022.
(Continued)

*Primary Examiner* — Niketa Patel
*Assistant Examiner* — Karmel J Webster
(74) *Attorney, Agent, or Firm* — Potomac Law Group, PLLC

(57) ABSTRACT

TTFields are applied using transducer arrays made from a plurality of individual electrode elements. The temperatures of those electrode elements can be normalized by positioning respective regions of pyroelectric material in thermal contact with the electrode elements, and subsequently applying an AC signal to each of the electrode elements at respective duty cycles so that an alternating electric field is induced within the subject. For each of the regions of the pyroelectric material, an electrical characteristic that is related to temperature is measured after the AC signal turns off. The duty cycles of the AC signals that are applied to the electrode elements is adjusted until the measured electrical characteristics indicate that the temperatures of all the regions of the pyroelectric material have equalized to within 1° C.

14 Claims, 8 Drawing Sheets

(58) Field of Classification Search
USPC ........................................................ 607/372
See application file for complete search history.

(56) References Cited

U.S. PATENT DOCUMENTS

| | | | |
|---|---|---|---|
| 7,016,725 B2 | 3/2006 | Palti | |
| 7,089,054 B2 | 8/2006 | Palti | |
| 7,136,699 B2 | 11/2006 | Palti | |
| 7,333,852 B2 | 2/2008 | Palti | |
| 7,467,011 B2 | 12/2008 | Palti | |
| 7,519,420 B2 | 4/2009 | Palti | |
| 7,565,205 B2 | 7/2009 | Palti | |
| 7,565,206 B2 | 7/2009 | Palti | |
| 7,599,745 B2 | 10/2009 | Palti | |
| 7,599,746 B2 * | 10/2009 | Palti | C12N 13/00 607/76 |
| 7,706,890 B2 | 4/2010 | Palti | |
| 7,715,921 B2 * | 5/2010 | Palti | A61N 1/0408 607/148 |
| 7,805,201 B2 | 9/2010 | Palti | |
| 7,890,183 B2 | 2/2011 | Palti et al. | |
| 7,912,540 B2 | 3/2011 | Palti | |
| 7,917,227 B2 | 3/2011 | Palti | |
| 8,019,414 B2 | 9/2011 | Palti | |
| 8,027,738 B2 | 9/2011 | Palti | |
| 8,170,684 B2 | 5/2012 | Palti | |
| 8,175,698 B2 | 5/2012 | Palti et al. | |
| 8,229,555 B2 | 7/2012 | Palti | |
| RE43,618 E | 8/2012 | Palti | |
| 8,244,345 B2 | 8/2012 | Palti | |
| 8,406,870 B2 | 3/2013 | Palti | |
| 8,447,395 B2 | 5/2013 | Palti et al. | |
| 8,447,396 B2 | 5/2013 | Palti et al. | |
| 8,465,533 B2 | 6/2013 | Palti | |
| 8,706,261 B2 | 4/2014 | Palti | |
| 8,715,203 B2 | 5/2014 | Palti | |
| 8,718,756 B2 | 5/2014 | Palti | |
| 8,764,675 B2 | 7/2014 | Palti | |
| 9,023,090 B2 | 5/2015 | Palti | |
| 9,023,091 B2 | 5/2015 | Palti | |
| 9,039,674 B2 | 5/2015 | Palti et al. | |
| 9,056,203 B2 | 6/2015 | Palti et al. | |
| 9,440,068 B2 | 9/2016 | Palti et al. | |
| 9,655,669 B2 | 5/2017 | Palti et al. | |
| 9,750,934 B2 | 9/2017 | Palti et al. | |
| 9,910,453 B2 | 3/2018 | Wasserman et al. | |
| 10,188,851 B2 | 1/2019 | Wenger et al. | |
| 10,441,776 B2 | 10/2019 | Kirson et al. | |
| 10,779,875 B2 | 9/2020 | Palti et al. | |
| 11,191,956 B2 | 12/2021 | Giladi et al. | |
| 2002/0161361 A1 * | 10/2002 | Sherman | A61B 18/1492 606/41 |
| 2005/0245857 A1 * | 11/2005 | Pizzi | A61K 47/6957 604/20 |
| 2006/0167499 A1 | 7/2006 | Palti | |
| 2007/0007863 A1 * | 1/2007 | Mohr, III | H10N 30/50 29/25.35 |
| 2007/0225766 A1 | 9/2007 | Palti | |
| 2007/0239213 A1 | 10/2007 | Palti | |
| 2009/0076366 A1 | 3/2009 | Palti | |
| 2010/0028969 A1 * | 2/2010 | Mueller | A61N 1/042 435/306.1 |
| 2011/0301683 A1 * | 12/2011 | Axelgaard | A61N 1/0492 607/149 |

| | | | |
|---|---|---|---|
| 2012/0029419 A1 | 2/2012 | Palti | |
| 2012/0283726 A1 | 11/2012 | Palti | |
| 2014/0330268 A1 | 11/2014 | Palti et al. | |
| 2016/0022986 A1 * | 1/2016 | Travers | A61N 1/32 |
| 2016/0284714 A1 * | 9/2016 | Park | C09D 127/16 |
| 2017/0120041 A1 | 5/2017 | Wenger et al. | |
| 2017/0215939 A1 | 8/2017 | Palti et al. | |
| 2017/0281934 A1 | 10/2017 | Giladi et al. | |
| 2018/0001075 A1 | 1/2018 | Kirson et al. | |
| 2018/0008708 A1 | 1/2018 | Giladi et al. | |
| 2018/0050200 A1 | 2/2018 | Wasserman et al. | |
| 2018/0160933 A1 | 6/2018 | Urman et al. | |
| 2018/0202991 A1 | 7/2018 | Giladi et al. | |
| 2018/0280687 A1 | 10/2018 | Carter et al. | |
| 2019/0117956 A1 | 4/2019 | Wenger et al. | |
| 2019/0117963 A1 | 4/2019 | Travers et al. | |
| 2019/0307781 A1 | 10/2019 | Krex et al. | |
| 2019/0308016 A1 | 10/2019 | Wenger et al. | |
| 2020/0001069 A1 | 1/2020 | Kirson et al. | |
| 2020/0009376 A1 | 1/2020 | Chang et al. | |
| 2020/0009377 A1 | 1/2020 | Chang et al. | |
| 2020/0016067 A1 | 1/2020 | Gotlib et al. | |
| 2020/0023179 A1 | 1/2020 | Bomzon et al. | |
| 2020/0061360 A1 | 2/2020 | Hagemann et al. | |
| 2020/0061361 A1 | 2/2020 | Hagemann et al. | |
| 2020/0069937 A1 | 3/2020 | Naveh et al. | |
| 2020/0078582 A1 | 3/2020 | Alon et al. | |
| 2020/0108031 A1 | 4/2020 | Borst et al. | |
| 2020/0114141 A1 | 4/2020 | Bomzon et al. | |
| 2020/0121728 A1 | 4/2020 | Wardak et al. | |
| 2020/0129761 A1 | 4/2020 | Bomzon et al. | |
| 2020/0146586 A1 | 5/2020 | Naveh et al. | |
| 2020/0155835 A1 * | 5/2020 | Wasserman | A61N 1/3603 |
| 2020/0171297 A1 | 6/2020 | Kirson et al. | |
| 2020/0179512 A1 | 6/2020 | Giladi et al. | |
| 2020/0219261 A1 | 7/2020 | Shamir et al. | |
| 2020/0269037 A1 | 8/2020 | Hagemann et al. | |
| 2020/0269041 A1 | 8/2020 | Zeevi et al. | |
| 2020/0368525 A1 | 11/2020 | Maag et al. | |
| 2021/0031031 A1 | 2/2021 | Wasserman et al. | |
| 2021/0038584 A1 | 2/2021 | Voloshin-Sela | |
| 2021/0060334 A1 | 3/2021 | Avraham et al. | |
| 2021/0069503 A1 | 3/2021 | Tran et al. | |
| 2021/0187277 A1 | 6/2021 | Wasserman et al. | |
| 2021/0196348 A1 | 7/2021 | Wasserman | |
| 2021/0199640 A1 | 7/2021 | Patel et al. | |
| 2021/0203250 A1 | 7/2021 | Wasserman | |
| 2021/0268247 A1 | 9/2021 | Story et al. | |
| 2021/0299440 A1 | 9/2021 | Deslauriers et al. | |
| 2021/0308446 A1 | 10/2021 | Alon et al. | |
| 2021/0330950 A1 | 10/2021 | Hagemann et al. | |
| 2021/0346694 A1 | 11/2021 | Wasserman et al. | |
| 2021/0379362 A1 | 12/2021 | Smith et al. | |
| 2021/0408383 A1 | 12/2021 | Kalra et al. | |
| 2022/0095997 A1 | 3/2022 | Wasserman | |
| 2022/0096821 A1 | 3/2022 | Kirson et al. | |
| 2022/0118249 A1 | 4/2022 | Bomzon et al. | |
| 2022/0161028 A1 | 5/2022 | Giladi et al. | |
| 2022/0193435 A1 | 6/2022 | Wasserman et al. | |

OTHER PUBLICATIONS

Partial International Search Report and Provisional Written Opinion issued in application PCT/IB2021/061665 dated Apr. 20, 2022.

* cited by examiner 40 (SUPPORT)

75 (SECOND ELECTRODE)

70 (PYROELECTRIC LAYER)

20 (FIRST ELECTRODE)

50 (HYDROGEL)

30 (INSULATING LAYER)

25 (FLEX PCB)

REAR    FRONT 60 (THERMISTOR)

75
20

40

Sc

F1 F2 F3 F4 F5 F6

10'

FRONT FACE 40 (SUPPORT)

75' (SECOND ELECTRODE)

70' (PYROELECTRIC SHEET)

120 (THIRD ELECTRODE)

110 (EXTRA INSULATING LAYER)

20 (FIRST ELECTRODE)

50 (HYDROGEL)

30 (INSULATING LAYER)

25 (FLEX PCB)

REAR          FRONT 60 (THERMISTOR)

75'
110
40
20

S1        F4        B
F1                  B

T1        S2        F5
F2        T2

S3        F6
F3

11

FRONT FACE

PYROELECTRIC-BASED TEMPERATURE SENSING OF TRANSDUCER ARRAYS FOR APPLYING TUMOR TREATING FIELDS (TTFIELDS)

CROSS REFERENCE TO RELATED APPLICATIONS

This Application claims the benefit of U.S. Provisional Application 63/126,911, filed Dec. 17, 2020, which is incorporated herein by reference in its entirety.

BACKGROUND

Tumor Treating Fields, or TTFields, are alternating electric fields within the intermediate frequency range (e.g., 100-500 kHz) that inhibit cancer cell growth. This non-invasive treatment targets solid tumors and is described in U.S. Pat. No. 7,565,205, which is incorporated herein by reference in its entirety. 200 kHz TTFields are FDA approved for the treatment of glioblastoma (GBM), and may be delivered, for example, via the prior art Optune™ system. Optune™ includes an electric field generator and two pairs of transducer arrays (i.e., electrode arrays) that are placed on the patient's shaved head. One pair of arrays (L/R) is positioned to the left and right of the tumor, and the other pair of arrays (A/P) is positioned anterior and posterior to the tumor. The Optune™ field generator (a) applies an AC voltage between the L/R transducer arrays (or electrodes) for 1 second; then (b) applies an AC voltage between the A/P transducer arrays (or electrodes) for 1 second; then repeats that two-step sequence (a) and (b) for the duration of the treatment.

U.S. Pat. No. 8,715,203 depicts a prior art design for these transducer arrays that uses a plurality of round ceramic elements. One side of each ceramic element is positioned against the patient's skin, and the other side of each ceramic element has a conductive backing. The conductive backings of all the ceramic elements in a given transducer array are all wired in parallel to a single conductor, and AC electrical signals are applied to this single conductor. The AC electrical signals are capacitively coupled into the patient's body through the ceramic elements. Thermistors are positioned in the center of some of the ceramic elements to sense the temperature at the skin beneath those ceramic elements. The Optune™ field generator inputs signals from those thermistors to determine the temperature of the transducer arrays. And if the system determines that the temperature has reached a threshold level, the system will reduce the AC voltage that is applied to the transducer arrays to prevent them from getting too hot.

SUMMARY OF THE INVENTION

Although the prior art approach of sensing the temperature of TTFields transducer arrays using a set of thermistors is workable, each thermistor requires its own dedicated wire within the cable that interconnects the transducer array with the field generator. More specifically, a transducer array that uses 8 thermistors to sense the temperature at various locations on the transducer array will require a cable with 10 conductors: one conductor for the TTFields signal; 8 conductors for the 8 thermistors, plus an additional conductor to serve as a return for all 8 thermistors. And the additional conductors that interface with the thermistors can make the cables thicker, less flexible, and more cumbersome. Further-more, each thermistor causes an incremental increase in the size, weight, and cost of the transducer arrays.

Further still, because all of the ceramic elements in any given conventional TTFields transducer array are wired in parallel to a single conductor, the Optune™ system cannot control the AC voltage that is applied to each electrode element on any given transducer array individually. As a result, if the temperature of only a single electrode element on a given transducer array has reached the threshold, the system must reduce the AC voltage that is applied to the entire transducer array to prevent the single electrode element from getting too hot.

The embodiments described herein rely on pyroelectric materials to sense the temperature of the electrode elements in TTFields transducer arrays. Some embodiments provide individual control of the AC signal that is applied to each electrode element on any given transducer array and also facilitates individual temperature-sensing for each electrode element, without unduly increasing the number of conductors in the transducer array's cable.

One aspect of the invention is directed to a first apparatus for applying an electric field to a living subject. The first apparatus comprises a plurality of first electrode elements and a plurality of first conductive leads. Each of the first electrode elements has a front face and a rear face, and each of the first conductive leads is disposed in electrical contact with a respective one of the first electrode elements. The first apparatus also comprises a plurality of regions of a pyroelectric material. Each of the regions of the pyroelectric material has a front face and a rear face, and the front face of each of the regions of the pyroelectric material is disposed in electrical and thermal contact with the rear face of the respective one of the first electrode elements. The first apparatus also comprises a plurality of second electrode regions, each of which contacts the rear face of a respective one of the regions of the pyroelectric material. The first apparatus also comprises at least one second conductive lead disposed in electrical contact with the plurality of second electrode regions, and at least one temperature sensor positioned in thermal contact with at least one of the first electrode elements.

In some embodiments of the first apparatus, each of the second electrode regions is non-contiguous with all other second electrode regions. The at least one second conductive lead comprises a plurality of conductive leads, each of which is disposed in electrical contact with a respective one of the second electrode regions. In some embodiments of the first apparatus, each of the second electrode regions is non-contiguous with all other second electrode regions, and the at least one second conductive lead comprises a single lead disposed in electrical contact with all the second electrode regions. In some embodiments of the first apparatus, all of the second electrode regions lie within a single sheet of conductive material, and the at least one second conductive lead is disposed in electrical contact with the single sheet of conductive material.

In some embodiments of the first apparatus, each of the regions of the pyroelectric material is non-contiguous with all other regions of the pyroelectric material. In some embodiments of the first apparatus, all of the regions of the pyroelectric material lie within a single sheet of pyroelectric material.

Some embodiments of the first apparatus further comprise a self-adhesive support structure configured to hold the front face of each of the first electrode elements against a portion of the subject's body. In some embodiments of the first apparatus, the at least one temperature sensor comprises at least one thermistor.

Some embodiments of the first apparatus further comprise a plurality of regions of a dielectric material with a dielectric constant of at least 20, and a self-adhesive support structure. Each of the regions of the dielectric material is disposed on the front face of a respective one of the first electrode elements. The self-adhesive support structure is configured to hold the front face of each of the first electrode elements against a portion of the subject's body with the regions of the dielectric material disposed between the front face of the first electrode elements and the subject's body. Optionally, these embodiments may further comprise a layer of hydrogel disposed between the regions of the dielectric material and the subject's body.

In some embodiments of the first apparatus, the areas of the plurality of first electrode elements collectively add up to at least 25 cm$^2$.

Another aspect of the invention is directed to a second apparatus for applying an electric field to a living subject. The second apparatus comprises a plurality of first electrode elements and a plurality of first conductive leads. Each of the first electrode elements has a front face and a rear face, and each of the first conductive leads is disposed in electrical contact with a respective one of the first electrode elements. The second apparatus also comprises a thermally conductive electrically insulating layer disposed on the rear face of each of the first electrode elements. The second apparatus also comprises a sheet of pyroelectric material that has a rear face and a front face. The sheet of pyroelectric material is positioned behind the electrically insulating layer and disposed in thermal contact with the first electrode elements. The second apparatus also comprises a plurality of second electrode regions positioned so that each of the second electrode regions makes electrical contact with a respective region of the rear face of the pyroelectric material. The second apparatus also comprises a plurality of second conductive leads, each of which is disposed in electrical contact with a respective one of the second electrode regions. The second apparatus also comprises a plurality of third electrode regions positioned so that each of the third electrode regions makes electrical contact with a respective region of the front face of the pyroelectric material. The third electrode regions are sandwiched between the pyroelectric material and the electrically insulating layer. The second apparatus also comprises a plurality of third conductive leads, each of which is disposed in electrical contact with a respective one of the third electrode regions.

In some embodiments of the second apparatus, each of the second electrode regions has a longitudinal axis, each of the third electrode regions has a longitudinal axis, and the longitudinal axes of the second electrode regions are substantially perpendicular to the longitudinal axes of the third electrode regions.

Some embodiments of the second apparatus further comprise a self-adhesive support structure configured to hold the front face of each of the first electrode elements against a portion of the subject's body.

Some embodiments of the second apparatus further comprise a plurality of regions of a dielectric material with a dielectric constant of at least 20 and a self-adhesive support structure. Each of the regions of the dielectric material is disposed on the front face of a respective one of the first electrode elements. And the self-adhesive support structure is configured to hold the front face of each of the first electrode elements against a portion of the subject's body with the regions of the dielectric material disposed between the front face of the first electrode elements and the subject's body. Optionally, these embodiments may further comprise a layer of hydrogel disposed between the regions of the dielectric material and the subject's body.

Some embodiments of the second apparatus further comprise at least one thermistor positioned in thermal contact with at least one of the first electrode elements. In some embodiments of the second apparatus, the areas of the plurality of first electrode elements collectively add up to at least 25 cm$^2$.

Another aspect of the invention is directed to a first method of normalizing temperatures of a plurality of first electrode elements positioned against a subject's body. Each of the first electrode elements is positioned in thermal contact with a respective region of a pyroelectric material. The first method comprises applying an AC signal to each of the first electrode elements at a respective duty cycle so that an alternating electric field is induced within the subject; and measuring, for each of the regions of the pyroelectric material, how an electrical characteristic that is a function of a change in temperature changes after the AC signal that is applied to each of the first electrode elements turns off. The first method also comprises adjusting the duty cycle of the AC signal that is applied to at least one of the first electrode elements until the measured electrical characteristics indicate that the temperatures of all the regions of the pyroelectric material have equalized to within 1° C.

In some instances of the first method, the adjusting comprises adjusting the duty cycle of the AC signal that is applied to the at least one of the first electrode elements until the measured electrical characteristics indicate that the temperatures of all the regions of the pyroelectric material have equalized to within 0.5° C., or, in some instances, to within 0.25° C.

In some instances of the first method, the adjusting comprises reducing the duty cycle of the AC signal that is applied to at least one first electrode element that is hotter than other first electrode elements.

Some instances of the first method further comprise determining a temperature of at least one of the first electrode elements. Optionally, in these embodiments, the determining of the temperature of the at least one of the first electrode elements comprises determining a temperature of at least one thermistor disposed in thermal contact with the at least one of the first electrode elements.

In some instances of the first method, the measuring comprises measuring, for each of the regions of the pyroelectric material, how a pyroelectric current changes after the AC signal that is applied to each of the first electrode elements turns off. Optionally, in these embodiments, the adjusting comprises reducing the duty cycle of the AC signal that is applied to at least one first electrode element that has a larger pyroelectric current than other first electrode elements.

Another aspect of the invention is directed to a third apparatus for normalizing temperatures of a plurality of first electrode elements when each of the first electrode elements is positioned in thermal contact with a respective region of a pyroelectric material. The third apparatus comprises an AC signal generator, a first plurality of switches, an amplifier, and a controller. The AC signal generator generates an AC output signal. The first plurality of switches is configured to switch the AC output signal to each of the first electrode elements on and then off at a respective duty cycle. The amplifier is configured to accept an electrical signal from each of the regions of the pyroelectric material and generate a corresponding set of output signals after the AC output signal that is applied to each of the first electrode elements switches off. And the controller is configured to accept the set of output signals and control the first plurality of switches so as to adjust the duty cycle of the AC output signal that is applied to at least one of the first electrode elements until the set of output signals indicate that the temperatures of all the regions of the pyroelectric material have equalized to within 1° C.

In some embodiments of the third apparatus, the controller is configured to control the first plurality of switches so as to adjust the duty cycle of the AC output signal that is applied to the at least one of the first electrode elements until the set of output signals indicate that the temperatures of all the regions of the pyroelectric material have equalized to within 0.5° C., or, in some embodiments, to within 0.25° C.

In some embodiments of the third apparatus, the controller is configured to (a) determine, based on the set of output signals, when at least one of the first electrode elements is hotter than other first electrode elements and (b) control the first plurality of switches so as to reduce the duty cycle of the AC output signal that is applied to the at least one first electrode element that is hotter than the other first electrode elements.

In some embodiments of the third apparatus, the controller is further configured to determine a temperature of at least one of the first electrode elements. Optionally, in these embodiments, the determination of the temperature of the at least one of the first electrode elements comprises inputting a signal from at least one thermistor disposed in thermal contact with the at least one of the first electrode elements.

Some embodiments of the third apparatus further comprise a second plurality of switches configured to sequentially switch the electrical signal from each of the regions of the pyroelectric material to the amplifier. Optionally, in these embodiments, each switch within the second plurality of switches has a first terminal and a second terminal; the first terminal of each of the second plurality of switches is connected to a respective terminal of a corresponding one of the first plurality of switches; and all the second terminals are connected to an input of the amplifier.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1:
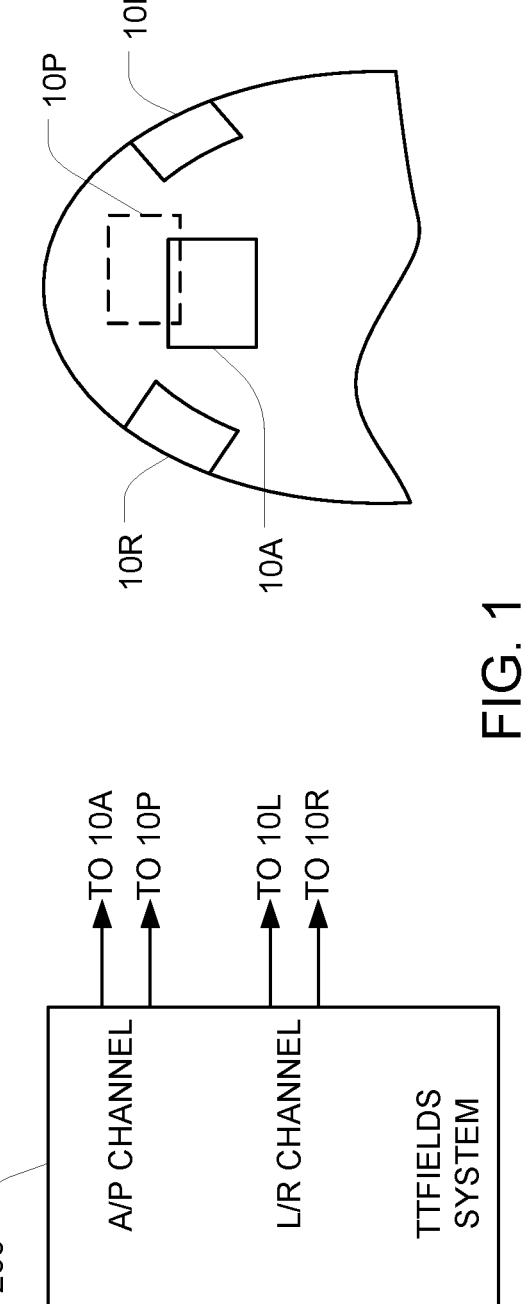
FIG. 1 is a system block diagram of an embodiment in which a TTFields system drives a set of TTFields transducer arrays with AC signals.

FIG. 1 is a system block diagram of an embodiment in which a TTFields system 200 drives a set of TTFields transducer arrays 10L, 10R, 10A, and 10P with AC signals at a frequency between 50 and 500 kHz or between 50 kHz and 1 MHz. One pair of transducer arrays (10L/10R) is positioned to the left and right of the tumor, and the other pair of transducer arrays (10A/10P) is positioned anterior and posterior to the tumor.

As described below in connection with FIGS. 2-3, each of the transducer arrays includes a plurality of individual electrode elements. And as described below in connection with FIG. 4, the TTFields system 200 (a) applies an AC voltage between selected electrode elements within the left transducer array 10L and selected elements within the right transducer array 10R for an interval of time (e.g., one second); then (b) applies an AC voltage between selected electrode elements within the anterior transducer array 10A and selected elements within the posterior transducer array 10P for the same interval of time; then repeats that two-step sequence (a) and (b) for the duration of the treatment.

The voltages generated by the TTFields system 200 during these steps (a) and (b) is preferably sufficient to induce an electric field of at least 1 V/cm in at least a portion of the tumor. In some embodiments, the voltages generated by the TTFields system 200 during these steps (a) and (b) is sufficient to induce an electric field of between 1 V/cm and 10 V/cm in at least a portion of the tumor.

Figures 2A, 2B:
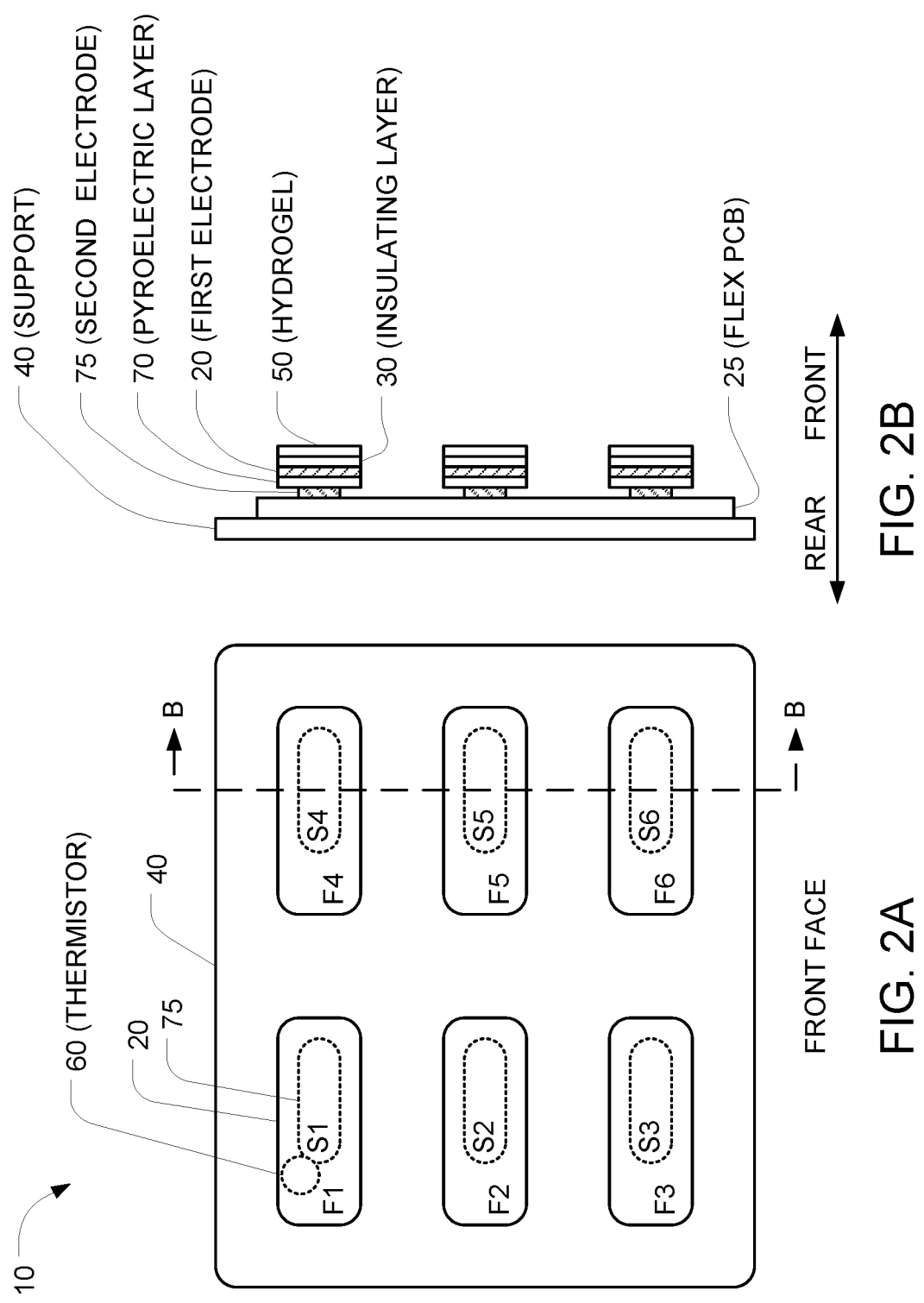
FIGS. 2A and 2B depict front and side views of an embodiment for implementing the transducer arrays depicted in FIG. 1.

FIGS. 2A and 2B depict front and side views of an embodiment for implementing any of the transducer arrays 10L, 10R, 10A, and 10P depicted in FIG. 1. Optionally, this embodiment may be constructed using a flex circuit. The FIG. 2A/2B embodiment is used for applying an electric field to a living subject, and it includes a plurality of first electrode elements 20. The first electrode elements are made from a conductive material (e.g., copper or another metal). Each of these first electrode elements 20 has a front face and a rear face. Note that although the example depicted in FIG. 2A/2B depicts only six first electrode elements 20 (labeled F1-F6) for simplicity, the actual number of first electrode elements 20 may vary from that value significantly (e.g., between 9 and 25, or between 4 and 50).

In contrast to the prior art Optune™ transducer arrays in which all of the electrode elements in any given transducer array are wired in parallel, the FIG. 2A/2B embodiment has a plurality of first conductive leads (not shown), and each of the first conductive leads is disposed in electrical contact with a respective one of the first electrode elements 20. These leads could be, for example, wires or traces on a PCB or flex circuit. And notably, because each of the first conductive leads corresponds to a respective one of the first electrode elements, it becomes possible to energize some of the electrode elements within any given transducer array without energizing all of the elements on that transducer array. This is accomplished by sending AC current into some (but not all) of the first conductive leads.

The FIG. 2A/2B embodiment also has a plurality of regions 70 of a pyroelectric material, which are used to determine the temperatures of corresponding first electrode elements 20 (labeled F1-F6) as described below in connection with FIGS. 5-6. Examples of suitable pyroelectric materials for forming the plurality of regions 70 include polyvinylidine fluoride (PVDF) homopolymers, PVDF organic derivatives e.g., poly-(vinylidine fluoride-trifluoro-ethylene) copolymers (P(VDF-TrFE)), and PVDF-ceramic composites. In some embodiments, the pyroelectric material is Piezotech® RT-FC, which is a P(VDF-TrFE) copolymer. Each of the regions 70 of the pyroelectric material has a front face and a rear face, and the front face of each of the regions 70 of the pyroelectric material is disposed in electrical and thermal contact with the rear face of the respective one of the first electrode elements 20. The electrical and thermal contact between the front face of each of the regions 70 of the pyroelectric material and the rear face of the respective one of the first electrode elements 20 may be achieved by placing those two faces in direct contact with each other (e.g., by depositing or spraying the first electrode elements 20 onto the regions 70 of the pyroelectric material during the manufacturing process). Alternatively, another layer of material that does not interrupt the electrical and thermal contact may be disposed between those two faces.

Figures 3A, 3B:
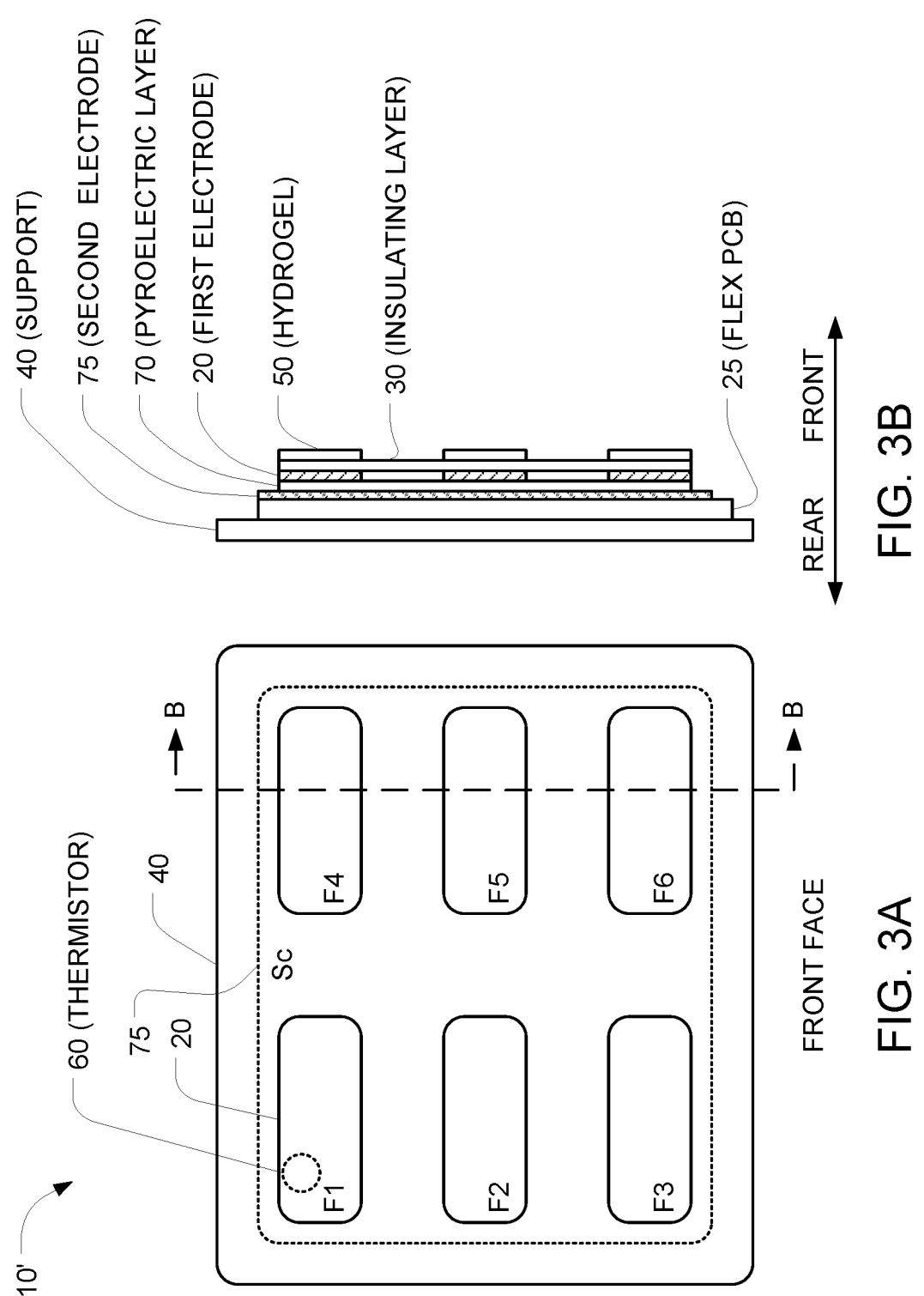
FIGS. 3A and 3B depict front and side views of another embodiment for implementing the transducer arrays depicted in FIG. 1.

Note that in some embodiments (e.g., as depicted in FIG. 2A/2B), each of the regions 70 of the pyroelectric material is non-contiguous with all other regions 70 of the pyroelectric material, so that the regions 70 resemble islands of material. But in alternative embodiments (e.g., as depicted in FIG. 3A/3B) all of the regions of the pyroelectric material lie within a single contiguous sheet of pyroelectric material.

The FIG. 2A/2B embodiment also has a plurality of second electrode regions 75, which are used to access corresponding regions 70 of the pyroelectric material in order to obtain temperature readings, as described below in connection with FIGS. 5-6. The second electrode regions 75 are formed from a conductive material (e.g., copper or another metal). Note that although the example depicted in FIG. 2A/2B depicts only six second electrode regions 75 (labeled S1-S6) for simplicity, the actual number of second electrode regions 75 may vary from that value significantly (e.g., between 9 and 25, or between 4 and 50). But the number of second electrode regions 75 is preferably the same as the number of first electrode elements 20.

Each of the second electrode regions 75 contacts the rear face of a respective one of the regions 70 of the pyroelectric material. And at least one second conductive lead (not shown) is disposed in electrical contact with the plurality of second electrode regions.

In some embodiments, the relationship in the previous paragraph may be accomplished by making each of the second electrode regions 75 non-contiguous with all other second electrode regions 75 (as depicted in FIG. 2A/2B) and by providing a plurality of conductive leads, each of which is disposed in electrical contact with a respective one of the second electrode regions (i.e., an individual second conductive lead for each respective second electrode regions 75). In alternative embodiments, the relationship in the previous paragraph may be accomplished by making each of the second electrode regions 75 non-contiguous with all other second electrode regions 75 (as depicted in FIG. 2A/2B) and by providing a single conductive lead disposed in electrical contact with all the second electrode regions 75 (thereby wiring all the second electrode regions 75 in parallel). In still other alternative embodiments, the relationship in the previous paragraph may be accomplished by having all of the second electrode regions lie within a single sheet of conductive material 75 (as depicted in FIG. 3A/3B), and by providing at least one second conductive lead disposed in electrical contact with the single sheet of conductive material.

The regions 70 of pyroelectric material can be used to determine the temperature of the first electrode elements 20 based on the following reasoning. Because each of the first electrode elements 20 (F1-F6) is disposed in thermal contact with a respective one of the regions 70 of the pyroelectric material, temperature variations of any given one of the first electrode elements 20 will cause a corresponding change in temperature in the respective region 70 of the pyroelectric material. This change in temperature will cause a pyroelectric voltage to appear across opposite faces of the respective region 70 of the pyroelectric material. The instantaneous value of this pyroelectric voltage can be measured via the first conductive leads (which are disposed in electrical contact with the first electrode elements 20) and the at least one second conductive lead (which is disposed in electrical contact with the plurality of second electrode regions 75). And due to the thermal contact between the first electrode elements 20 and the respective region 70 of the pyroelectric material, the measured electrical signals not only represent the change in temperature of each region 70 of the pyroelectric material—they also represent the change in temperature of each respective one of the first electrode elements 20. These changes in temperature are eventually used to prevent any of the first electrode elements 20 from overheating, as described below in connection with FIGS. 5-6.

The pyroelectric voltage that appears across any given region 70 of the pyroelectric material can be determined by measuring the voltage between the respective first electrode element 20 and the respective second electrode region 75. Alternatively, a pyroelectric current can be measured by measuring the current that flows through the respective first electrode element 20 and the respective second electrode region 75. And because this can be done for each of the first electrode elements 20, temperature information for each of the first electrode elements 20 becomes available to the TTFields system 200 described below in connection with FIG. 4 (via the plurality of first conductive leads and the at least one second conductive lead).

With this arrangement, each individual first conductive lead serves two functions. First, it provides an AC signal to a respective one of the first electrode elements 20, and this AC signal is used to impose TTFields in the subject's body. And second, it is used to sense the temperature change of the respective first electrode element 20 based on the pyroelectric effect described immediately above.

In some embodiments, each of the first electrode elements 20 is positioned against the subject's body so that there is an electrically conductive path between each of the first electrode elements 20 and the subject's body (e.g., by positioning the first electrode elements 20 directly against the subject's body, or by positioning the first electrode elements 20 against the subject's body with a layer of hydrogel disposed between the first electrode elements 20 and the subject's body).

But in alternative embodiments, the first electrode elements 20 are capacitively coupled to the subject's body, in which case an insulating dielectric layer is interposed between each of the first electrode elements 20 and the subject's body. In these embodiments, each transducer array includes a plurality of regions 30 of a dielectric material (i.e., an insulating material). Each of these regions 30 of the dielectric material is disposed on the front face of a respective one of the first electrode elements 20 so that it is interposed between the respective first electrode element 20 and the subject's body. In these embodiments, the regions 30 of the dielectric material may be positioned directly against the subject's body. Alternatively, the regions 30 of the dielectric material may be positioned against the subject's body with a layer of hydrogel disposed between the regions 30 of the dielectric material and the subject's body.

In some preferred embodiments, the regions 30 of dielectric material are discrete sections of a flexible polymer that are separated by gaps, as depicted in FIG. 2A/2B. Alternatively, the regions 30 of dielectric material could be regions within a single contiguous sheet of a flexible polymer material, as depicted in FIG. 3A/3B.

When a flexible polymer is used to implement the regions 30 of the dielectric material, suitable specifications for the flexible polymer are as follows: (1) at at least one frequency between 100 kHz and 500 kHz, each of the regions 30 has a dielectric constant of at least 20; and (2) each of the regions 30 has a thickness of less than 20 μm in a direction perpendicular to its front face. In some embodiments, the thickness of each of the regions 30 multiplied by its dielectric strength is at least 50 V, and in some embodiments this value is at least 200 V. For example, if the thickness is 10 μm and the dielectric strength is 5 V/μm, the product of the thickness and the dielectric strength would be 50 V. Or if the thickness is 10 μm and the dielectric strength is 20 V/μm, the product would be 200 V.

In some preferred embodiments, the polymer layer 30 comprises poly(vinylidene fluoride-trifluoroethylene-chlorotrifluoroethylene) and/or poly(vinylidene fluoride-trifluoroethylene-1-chlorofluoroethylene). Those two polymers are abbreviated herein as "Poly(VDF-TrFE-CtFE)" and "Poly (VDF-TrFE-CFE)", respectively. Optionally, ceramic nanoparticles may be mixed into the Poly(VDF-TrFE-CtFE) and/or Poly(VDF-TrFE-CFE) to form a "nanocomposite." Optionally, these ceramic nanoparticles may comprise ferroelectric metal oxides (e.g., at least one of barium titanate and barium strontium titanate).

In alternative embodiments, a different polymer that provides a high level of capacitance may be used. Example of alternative polymers that may be used in place of Poly(VDF-TrFE-CtFE) and/or Poly(VDF-TrFE-CFE) include the following: (1) ceramic nanoparticles mixed into at least one of Poly(VDF-TrFE), P(VDF-HFP), PVDF, or other polymers (where HFP is hexafluoropropylene); and (2) barium titanate and/or barium strontium titanate ceramic nanoparticles mixed into at least one of Poly(VDF-TrFE), P(VDF-HFP), PVDF. In other embodiments, the polymer layer 30 is formed by mixing ceramic nanoparticles into at least one other polymer.

In those embodiments that implement the plurality of regions 30 of dielectric material using flexible polymer regions, the polymer regions can be printed, sprayed, or cast directly onto the first electrode elements 20, which makes it much easier to obtain a very thin polymer layer. In some embodiments (e.g., in those embodiments where the polymer regions 30 are printed, sprayed, or cast directly onto the first electrode elements 20), the polymer regions have a thickness of less than 5 μm.

Increasing the total area that is covered by the first electrode elements 20 can be advantageous. In some embodiments, the areas of the plurality of first electrode elements 20 collectively add up to at least 25 cm².

Optionally, a self-adhesive support structure 40 may be incorporated into each transducer array 10. This self-adhesive support structure 40 is configured to hold the front face of each of the first electrode elements 20 against a portion of the subject's body with the regions 30 of the dielectric material disposed between the front face of the first electrode elements 20 and the subject's body. Optionally, these embodiments further comprise a layer of hydrogel 50 disposed between the regions 30 of the dielectric material and the subject's body. In those embodiments that do not include regions 30 of the dielectric material, the self-adhesive support structure is configured to hold the front face of each of the first electrode elements 20 against a portion of the subject's body (optionally with a layer of hydrogel interposed between the front face of each of the first electrode elements 20 and the subject's body).

The FIG. 2A/2B embodiment also has at least one temperature sensor positioned in thermal contact with at least one of the first electrode elements. In some preferred embodiments, the temperature sensor is a thermistor 60. Both terminals of the thermistor are made accessible via appropriate conductors. Optionally, in those embodiments in which a single lead is disposed in electrical contact with all the second electrode regions 75, one terminal of the thermistor 60 may be electrically connected to that same single lead.

One approach for building the FIG. 2A/2B embodiment is to begin with a flex PCB substrate 25. The plurality of second electrode regions 75 are then deposited on the flex PCB substrate 25. The plurality of regions 70 of the pyroelectric material are then deposited on the second electrode regions 75. The plurality of first electrode elements 20 are then deposited on the plurality of regions 70 of the pyroelectric material. In those embodiments that include a plurality of regions of a dielectric material, the plurality of regions 30 of the dielectric material are then deposited on the plurality of the first electrode elements 20. Optionally, a layer of hydrogel 50 is then applied on the plurality of regions 30 of the dielectric material. Finally, a support structure 40 is affixed to the rear face of the flex PCB substrate 25.

Note that in the FIG. 2A/2B embodiment, the plurality of regions 70 of the pyroelectric material are noncontiguous, such that each of the plurality of regions 70 of the pyroelectric material does not touch any other region of pyroelectric material. Similarly, the plurality of second electrode regions 75 are noncontiguous, such that each of the plurality of second electrode region 75 does not touch any other second electrode region. Similarly, the plurality of regions 30 of the dielectric material are noncontiguous, such that each of the plurality of regions 30 of the dielectric material does not touch any other region of dielectric material. But in alternative embodiments, one or more of these three items may be replaced by a contiguous sheet, as described below in connection with FIG. 3A/3B.

FIGS. 3A and 3B depict front and side views of another embodiment for implementing any of the transducer arrays 10L, 10R, 10A, and 10P depicted in FIG. 1. This embodiment is similar to the FIG. 2A/2B embodiment described above, except that each of the three items discussed in the preceding paragraph is replaced by a contiguous sheet. More specifically, the plurality of individual noncontiguous regions 70 of pyroelectric material in the FIG. 2A/2B embodiment are replaced with a single sheet of pyroelectric material, and regions within that single sheet serve as the plurality of regions of the pyroelectric material. Similarly, the plurality of individual noncontiguous second electrode region 75 in the FIG. 2A/2B embodiment are replaced with a single conductive sheet 75 (labeled SC), and regions within that single sheet SC serve as the plurality of second electrode regions. And similarly, the plurality of individual noncontiguous regions 30 of the dielectric material are replaced with a single sheet of a dielectric material (e.g., a flexible polymer).

Note that when a single conductive sheet 75 serves as the plurality of second electrode regions, it is preferable to use a single second conductive lead disposed in electrical contact with that single conductive sheet 75, instead of using a plurality of second conductive leads and disposing all of those second conductive leads in electrical contact with the same single conductive sheet. But the latter configuration is also acceptable.

Figure 4:
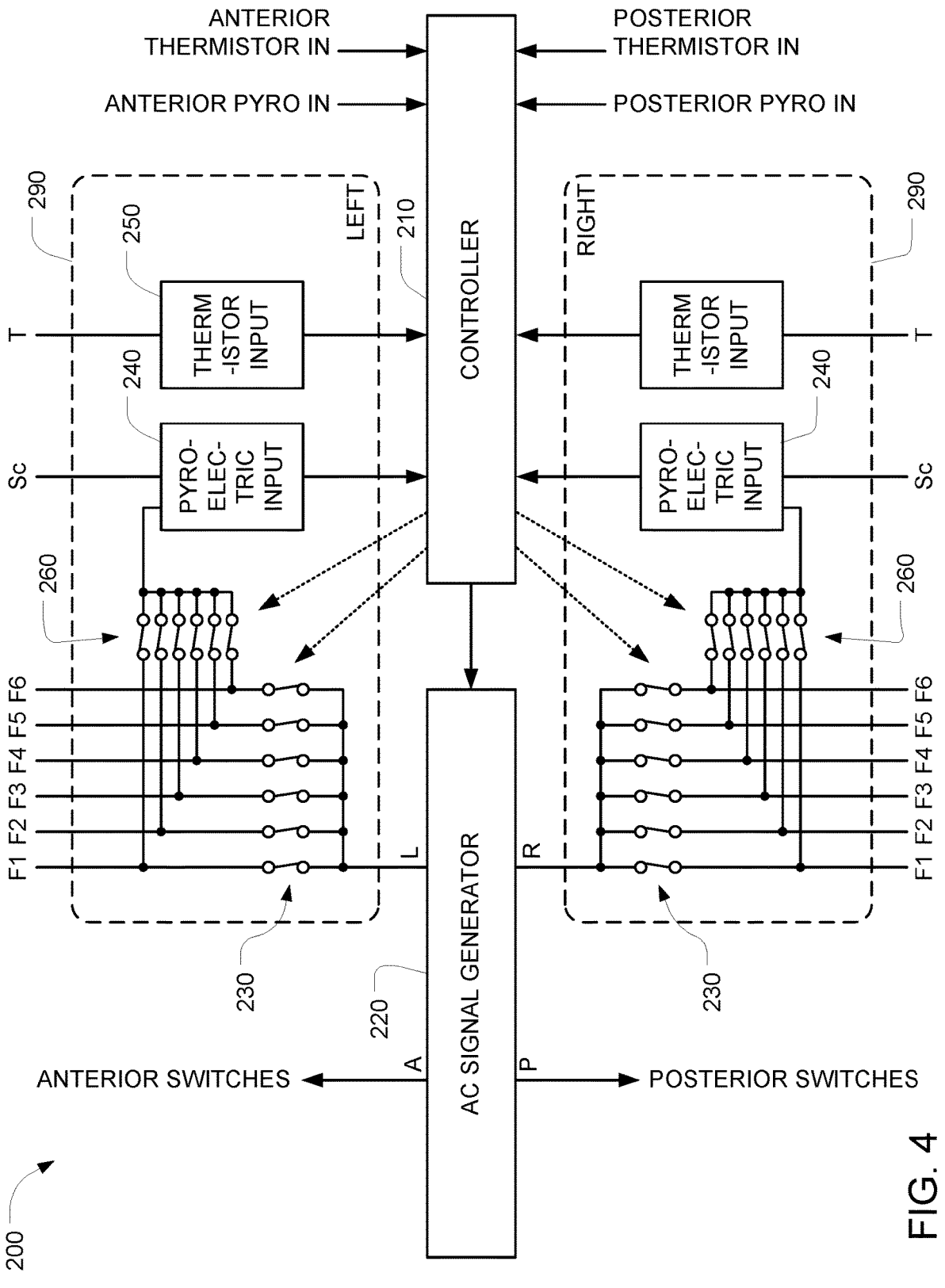
FIG. 4 depicts an embodiment of a TTFields system that is designed to interface with the transducer arrays depicted in FIGS. 2 and 3.

FIG. 4 depicts an embodiment of a TTFields system 200 that is designed to interface with the transducer arrays 10 depicted in FIGS. 2 and 3. The configuration depicted in FIG. 4 is a two-channel configuration. One channel is used to apply AC signals between the left and right transducer arrays 10L/10R (depicted in FIG. 1), and the other channel is used to apply AC signals between the anterior and posterior transducer arrays 10A/10P. Note that FIG. 4 only shows details 290 of the circuitry for the left and right channels, and the discussion below focuses on those channels. But the circuitry and operation of the anterior and posterior channels is the same as for the left and right channels. Note also that in alternative embodiments, the system 200 may have only a single channel, in which case it would drive only a single pair of transducer arrays 10 instead of two pairs of transducer arrays 10.

A controller 210 is configured to control all of the operations described herein. In some preferred embodiments, the controller 210 is implemented using a microprocessor or microcontroller that executes program instructions to control all of the operations described herein.

An AC signal generator 220 in the illustrated embodiment has one AC output for the L/R channel and a second AC output for the A/P channel. In some preferred embodiments, the AC signal generator 220 may be constructed as described in U.S. Pat. No. 9,910,453, which is incorporated herein by reference in its entirety. But a wide variety of alternative configurations for the AC signal generator 220 can be readily envisioned by persons skilled in the relevant arts.

Unlike the prior art Optune™ system (in which the output of the AC signal generator is always applied to all elements in any given transducer array by a single conductor), the transducer arrays 10 described herein have a plurality of first electrode elements 20 (labeled F1-F6), each of which has a corresponding first conductive lead (as described above).

The system 200 relies on a first plurality of switches 230 to switch the AC output signal to each of the first electrode elements 20 on or off. The conductors that lead to each of the first electrode elements 20 are labeled F1-F6 and appear at the top and bottom of FIG. 4 (for the left and right channels, respectively). The switches 230 are preferably implemented using an electronic switch (e.g., a solid-state relay or field effect transistor), the construction of which will be apparent to persons skilled in the relevant arts.

Each of the switches 230 is controlled to be either in the on state or the off state based on signals that are generated by the controller 210. When any given one of the switches 230 is on, that switch allows current to reach a respective one of the first electrode elements 20 in the respective transducer array 10. Conversely, when any given one of the switches 230 is off, that switch will prevent current from reaching that particular first electrode element 20.

As explained above in connection with FIGS. 2 and 3, each of the transducer arrays 10 has a plurality of first electrode elements 20, and each of those first electrode elements 20 is positioned in thermal contact with a respective region 70 of a pyroelectric material. In addition, as explained above, both faces of each region 70 of the pyroelectric material are electrically accessible via the first electrode elements 20 and the second electrode regions 75.

All of the second electrode region 75 in any given transducer array 10 are wired together in parallel (e.g., using one or more wires, or by using a single conductive sheet that includes all of the second electrode regions); and this parallel connection is wired to the common terminal (labeled SC in FIG. 4) of the amplifier 240 for the corresponding channel (i.e., the left or right channel).

The amplifier 240 is configured to accept an electrical signal from each of the regions 70 of the pyroelectric material and generate a corresponding set of output signals, which are provided to the controller 210. One approach for accomplishing this is to use a second plurality of switches 260 configured to sequentially switch the electrical signal from each of the regions 70 of the pyroelectric material to the amplifier 240 in turn. Each of the switches 260 is controlled to be either in the on state or the off state based on signals that are generated by the controller 210.

Each switch within the second plurality of switches 260 has a first terminal and a second terminal (on the left and right of FIG. 4, respectively). The first terminal of each of the second plurality of switches 260 is connected to a respective one of the first electrode elements 20 (F1-F6), and all the second terminals are connected to the input of the amplifier 240.

When this configuration is used and the uppermost switch in bank 260 in the left channel is closed and the remaining switches in bank 260 are open, the signal from one of the first electrode elements 20 (F1) is routed to the input of the amplifier 240. And when the next switch in bank 260 is closed and the remaining switches and bank 260 are open, the signal from another one of the first electrode elements 20 (F2) is routed to the input of the amplifier 240.

Using the second plurality of switches 260 is advantageous because it provides isolation. But in alternative embodiments, a multiplexor may be used in place of the second plurality of switches 260, in which case isolation would be sacrificed. In other alternative embodiments, the amplifier 240 may be replaced by a multi-channel amplifier that includes a separate channel dedicated to each of the first electrode elements 20.

As explained above in connection with FIGS. 2 and 3, each of the transducer arrays 10 has a thermistor. And each channel of the system 200 has an analog circuit 250 configured to interface with the thermistor. An output of this analog circuit 250 is provided to the controller 210.

When the transducer arrays 10 are positioned against a person's body, the system 200 can be used to treat a tumor within the person's body using TTFields. The system 200 includes two channels: a left/right (L/R) channel and an anterior/posterior (A/P) channel. Application of TTFields to a person's body using these two channels proceeds in an alternating sequence. In the first phase of the sequence, TTFields are applied using the L/R channel for a duration of time (e.g., one second). Then, in the second phase of the sequence, TTFields are applied using the A/P channel for the same duration of time. Then, this two-phase sequence repeats for the duration of the treatment. Temperature measurements in any given channel are preferably made during times when TTFields are not being applied for that particular channel. For example, temperature measurements for the L/R channel may be made while the A/P channel is actively delivering TTFields, and vice versa.

Let us first examine the situation when the L/R channel is used to apply TTFields, and every one of the first electrode elements 20 is operating at its maximum duty cycle. The controller 210 sets this situation up by sending signals to close all of the first plurality of switches 230 in the left channel and to close all of the first plurality of switches 230 in the right channel. The AC signal generator 220 applies an AC signal across its L and R outputs. The AC signal travels through all the switches within the first plurality of switches 230 in the left channel and arrives at each of the plurality of first electrode elements 20 within the left transducer array 10L. Meanwhile, the AC signal travels through all the switches within the first plurality of switches 230 in the right channel and arrives at each of the plurality of first electrode elements 20 within the right transducer array 10R. Because those transducer arrays 10L, 10R are positioned against the subject's body, AC current is coupled (e.g., capacitively coupled) into the person's body, and TTFields are induced within the person's body. Eventually, when the 1 second L/R phase ends, the AC signal generator 220 turns off its L/R output and turns on its A/P output.

Figure 5:
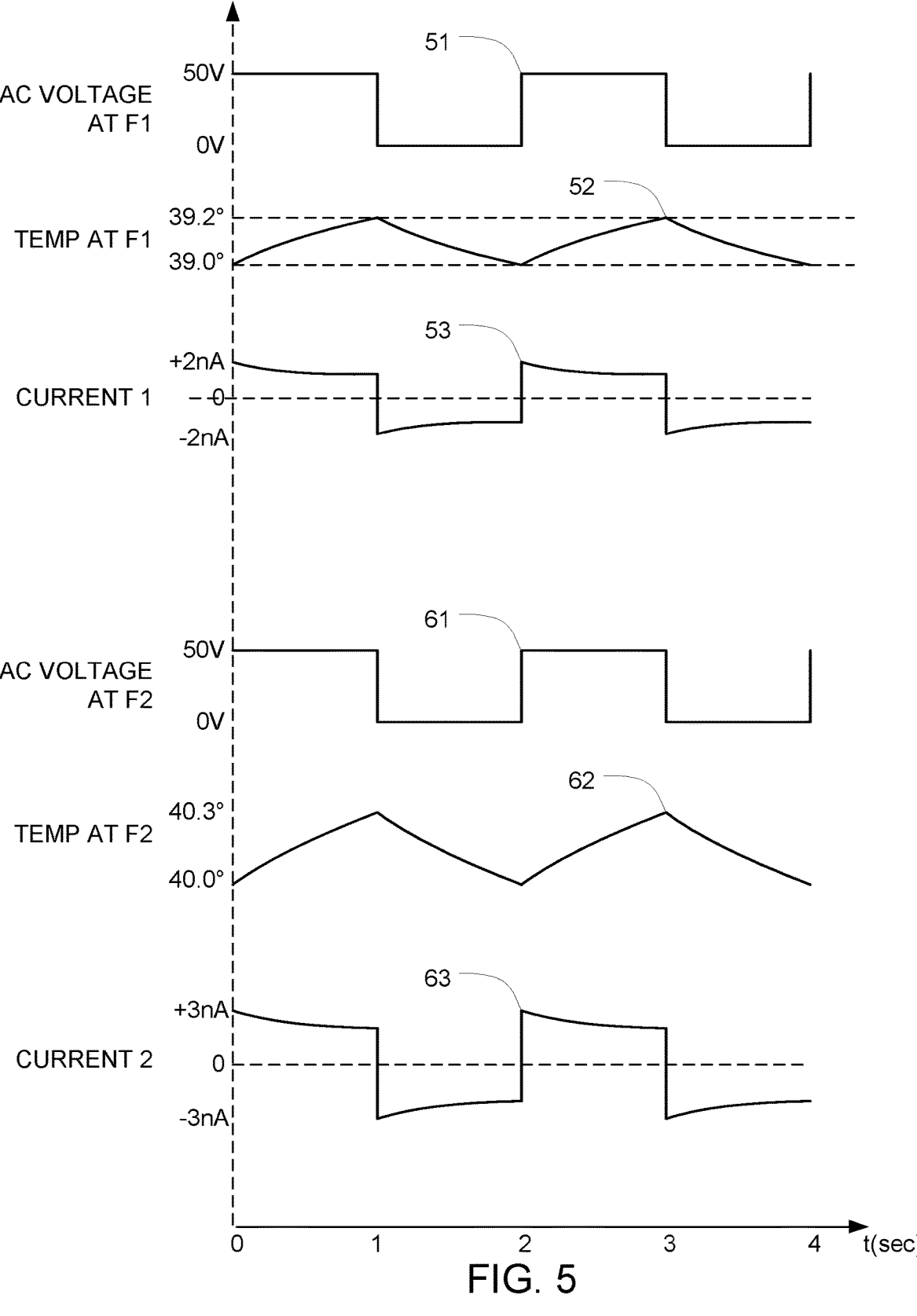
FIG. 5 depicts the electrical and thermal events that occur within one of the transducer arrays under a first set of conditions.

FIG. 5 depicts the electrical and thermal events that flow from the situation described in the previous paragraph at two of the first electrode elements 20 (F1 and F2) within one of the transducer arrays. More specifically, traces 51 and 61 depict the AC voltages that are applied to electrode elements F1 and F2. The AC voltage at each of these electrode elements has a 50% duty cycle (i.e., on for one second and off for one second) because any given electrode element in a given transducer array (e.g., 10L) is only active when the corresponding channel (e.g., the L/R channel) is being used to apply TTFields.

When any given one of the switches 230 is on, current will reach a respective one of the first electrode elements 20 in the respective transducer array, and that will cause the temperature of the respective first electrode element 20 to rise. Immediately after any given one of the switches 230 turns off, current will no longer reach the respective first electrode elements 20, and that will cause the temperature of the respective first electrode element 20 to drop (until the current turns on again). Traces 52 and 62 represent the instantaneous temperature of the electrode elements F1 and F2 that results from switching the current on and off at a 50% duty cycle. (Note that the numeric values in this example are provided for illustrative purposes only, and the actual temperature values and fluctuations may vary.)

Let us assume that electrode element F2 is running hotter than electrode element F1 (as depicted in traces 62 and 52). Whenever a given electrode element is running hotter than another electrode element, two things will occur: First, the average absolute temperature of the given electrode element will be higher than the average temperature of the other electrode element. And second, the temperature fluctuations of the given electrode element will also be larger than the temperature fluctuations of the other electrode element. Traces 52 and 62 depict examples of both of these conditions because the average temperature at element F1 is 39.1° C. while the average temperature at element F2 is 40.15° C.; and because the temperature fluctuations at element F1 traverses a range of 0.2° C. while the temperature fluctuations at element F2 traverses a range of 0.3° C.

If a given electrode element is operating at a higher temperature than the other electrode elements, the given electrode element will have correspondingly larger temperature fluctuations than the other electrode elements. And if any two electrode elements are operating at the same temperature, the temperature fluctuations of those two electrode elements will be the same. Conversely, when the temperature fluctuations of any two electrode elements are the same, one can conclude that the temperatures of those two electrode elements are the same. Similarly, when the temperature fluctuations of any two electrode elements are sufficiently close, one can conclude that the temperatures of those two electrode elements deviate by less than 1° C. And when the temperature fluctuations of any two electrode elements are even closer, one can conclude that the temperatures of those two electrode elements deviate by less than 0.5° C., or even less than 0.25° C.

Pyroelectric materials do not generate an output based on their absolute temperature. Instead, they generate an electrical output that is a function of a change in temperature. First electrode elements 20 (F1-F6, which includes F1 and F2) are each positioned in thermal contact with a respective region 70 of pyroelectric material with similar characteristics. So if electrode element F2 is running hotter than electrode element F1, the temperature fluctuations at electrode element F2 will be larger than the temperature fluctuations at electrode element F1. And this will cause the region 70 of pyroelectric material positioned in contact with the electrode element F2 to generate a larger electrical output than the region 70 of pyroelectric material positioned in contact with the electrode element F1. See, e.g., traces 53 and 63 which show that current 2 is larger than current 1. (Here again, the numeric values are provided for illustrative purposes only.) Note that while FIG. 5 describes this situation in the context of current, a corresponding voltage could be used in place of current.

The controller 210 can compare the temperature fluctuations of all the first electrode elements 20 (e.g., F1-F6) by sampling the signals that are generated by the regions 70 of pyroelectric material that are positioned in thermal contact with those electrode elements during a window of time after the AC signal that is applied to each of the first electrode elements 20 turns off (e.g., between t=1 and t=2 in FIG. 5). This may be implemented, for example, by sequentially closing each of the second plurality of switches 260 in turn to sequentially route the signal from each of the region 70 of pyroelectric material to the amplifier 240 in turn, capturing the output of the amplifier 240, and then repeating this sampling at a fast enough rate to track the temperature change (e.g., by repeating the sampling of all inputs every 5 ms). The controller 210 then determines, for each of the regions of the pyroelectric material, how the electrical characteristic (e.g., current or voltage) changes during a window of time after the AC signal that is applied to each of the first electrode elements turns off.

By analyzing how the electrical characteristic (i.e., traces 53 and 63) change over time, the controller 210 can determine that the temperature fluctuations of a given first electrode element 20 (e.g., F2) are larger than the temperature fluctuations of another first electrode element 20 (e.g., F1). The controller 210 can then use this information to normalize the temperature fluctuations of the first electrode elements 20 by adjusting the duty cycle of the AC signal that is applied to at least one of the first electrode elements 20 until the measured electrical characteristics indicate that the temperature fluctuations are such that the temperatures of all the regions of the pyroelectric material have equalized to within 1° C. In some embodiments, the controller 210 adjusts the duty cycle until the measured electrical characteristics indicate that the temperature fluctuations are such that the temperatures of all the regions of the pyroelectric material have equalized to within 0.5° C. or within 0.25° C.

Let us assume that the controller 210 has determined that the temperature fluctuations of a given first electrode element 20 (e.g., F2/trace 63) are larger than the temperature fluctuations of another first electrode element 20 (e.g., F1/trace 53). The controller 210 can normalize the temperature between those two electrode elements by reducing the duty cycle of the AC signal that is applied to the first electrode element F2 (which is hotter than first electrode element F1).

Figure 6:
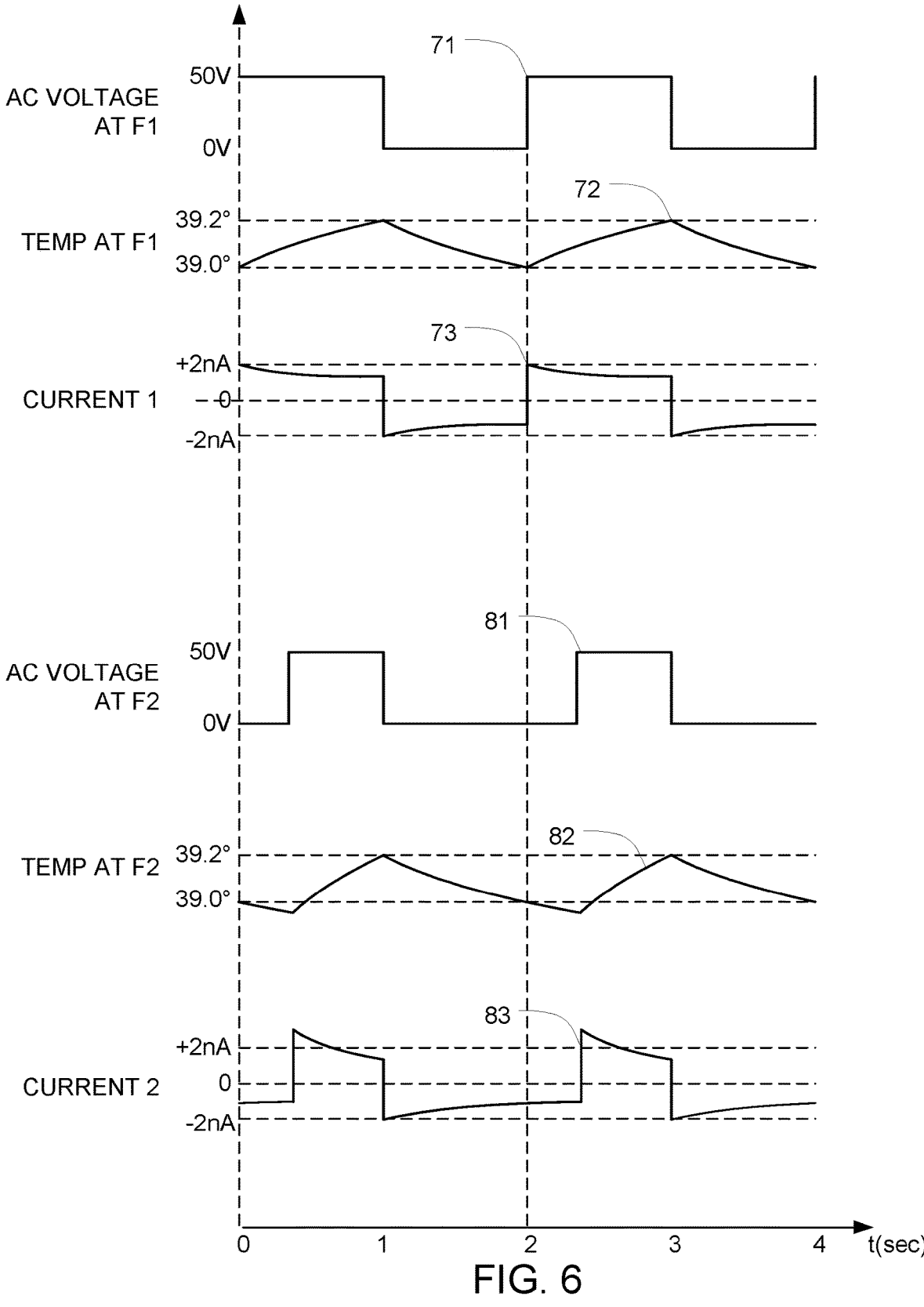
FIG. 6 depicts the electrical and thermal events that occur within one of the transducer arrays under a second set of conditions.

FIG. 6 depicts what happens after the controller 210 recognizes the situation described above in connection with FIG. 5, and subsequently (a) reduces the duty cycle of the AC signal that is applied to the first electrode element F2 from 50% to 33%; and (b) waits a long enough time (e.g., 30 s) for that electrode element F2 to cool down. Note that the reduction in duty cycle is preferably synchronized so that the AC signal that is applied to all of the first electrode elements turn off simultaneously. The situation for one of the first electrode elements 20 (F1) in FIG. 6 remains the same as it was in FIG. 5, and as a result traces 71-73 in FIG. 6 are the same as traces 51-53 in FIG. 5. But because the other first electrode element 20 (F2) is now being driven at a lower duty cycle (see trace 81), its absolute temperature will drop, and its range of temperature fluctuations will also drop (see trace 82).

The controller 210 compares the temperature fluctuations of all the first electrode elements 20 (e.g., F1-F6) by sampling the signals that are generated by the regions 70 of pyroelectric material as described above in connection with FIG. 5 (see traces 73 and 83). The controller 210 then determines, for each of the regions of the pyroelectric material, how the electrical characteristic (e.g., current or voltage) changes during a window of time after the AC signal that is applied to each of the first electrode elements turns off (e.g., between t=1 and t=2 in FIG. 6). If the adjustment in duty cycle was sufficient to equalize the temperature fluctuations of the first electrode elements 20 (as depicted in FIG. 6), the controller 210 can ascertain that the temperatures have equalized by comparing the electrical characteristics during the window of time that follows turning off the AC signal, and detecting similar fluctuations. (Note how the portions of the temperature traces 72, 82 between t=1 and t=2 are similar, as are the corresponding portions of the electrical traces 73, 83.)

If the adjustment in duty cycle was insufficient to equalize the temperature of the first electrode elements 20, the controller 210 can make a further reduction in duty cycle. If, on the other hand, the adjustment in duty cycle caused the temperature fluctuations of a given one of the first electrode elements 20 (e.g., F2) to become smaller than the temperature fluctuations of other first electrode elements 20, the controller 210 can dial back the reduction in duty cycle for the given one of the first electrode elements 20. (Note that the two situations described in this paragraph are not depicted in FIG. 6.)

Because pyroelectric materials respond to changes in temperature (as opposed to absolute temperature), a pyroelectric material that is cycling between 37° C. and 37.2° C. will produce the same output as when that same pyroelectric material is cycling between 40° C. and a 40.2° C. In view of this, it is not sufficient to merely equalize the temperature of all the first electrode elements 20 within any given transducer array as described above. To the contrary—because the temperature of transducer arrays should be maintained below a given threshold (e.g., 39° C.), one more piece of information is needed to ensure that the transducer arrays do not overheat. And this additional piece of information is the absolute temperature of at least one of the first electrode elements 20. For if the absolute temperature of a single one of the first electrode elements 20 is known, and it is also known that the temperatures of all of the first electrode elements 20 are all within a given tolerance (e.g., 1° C., 0.5° C., 0.25° C., etc.), we can then ensure that none of the first electrode elements 20 are hotter than the threshold temperature.

In view of this, at least one temperature sensor is positioned in thermal contact with at least one of the first electrode elements. In some embodiments, a single thermistor 60 is positioned in thermal contact with a single one of the first electrode elements 20 (e.g., element F1), as depicted in FIGS. 2 and 3. In alternative embodiments, more than one thermistor may be positioned in thermal contact with more than one of the first electrode elements 20. In other alternative embodiments, a temperature sensor other than a thermistor (e.g., an RTD or an AD590 integrated circuit) may be used.

The system 200 depicted in FIG. 4 includes an analog circuit 250 (e.g., an amplifier) for conditioning the signal from the thermistor 60 and providing an output to the controller 210, so that the controller 210 can determine the temperature of the thermistor 60 (and thereby determine the temperature of the first electrode elements 20 that is in thermal contact with the thermistors 60).

As explained above, application of TTFields to a person's body in a two channel device proceeds in an alternating sequence. In the first phase of the sequence, TTFields are applied using the L/R channel; and in the second phase of the sequence, TTFields are applied using the A/P channel. Then, this two-phase sequence repeats for the duration of the treatment. In the FIGS. 2 and 3 embodiments described above, each of the first electrode elements 20 in the transducer arrays 10L, 10R performs two functions: (a) it is used for applying TTFields to the subject when AC voltages are applied to the first electrode elements 20 during the first phase of the sequence; and (b) it is used to sense the electrical characteristics of the regions 70 of pyroelectric material that are disposed in electrical contact with the same first electrode elements 20 (in order to sense the temperature of the first electrode elements 20). But in alternative embodiments, the TTFields-application and temperature-sensing functions can be performed by separate (i.e., non-shared) structures within each transducer array, as described below in connection with FIGS. 7A/7B.

Figures 7A, 7B:
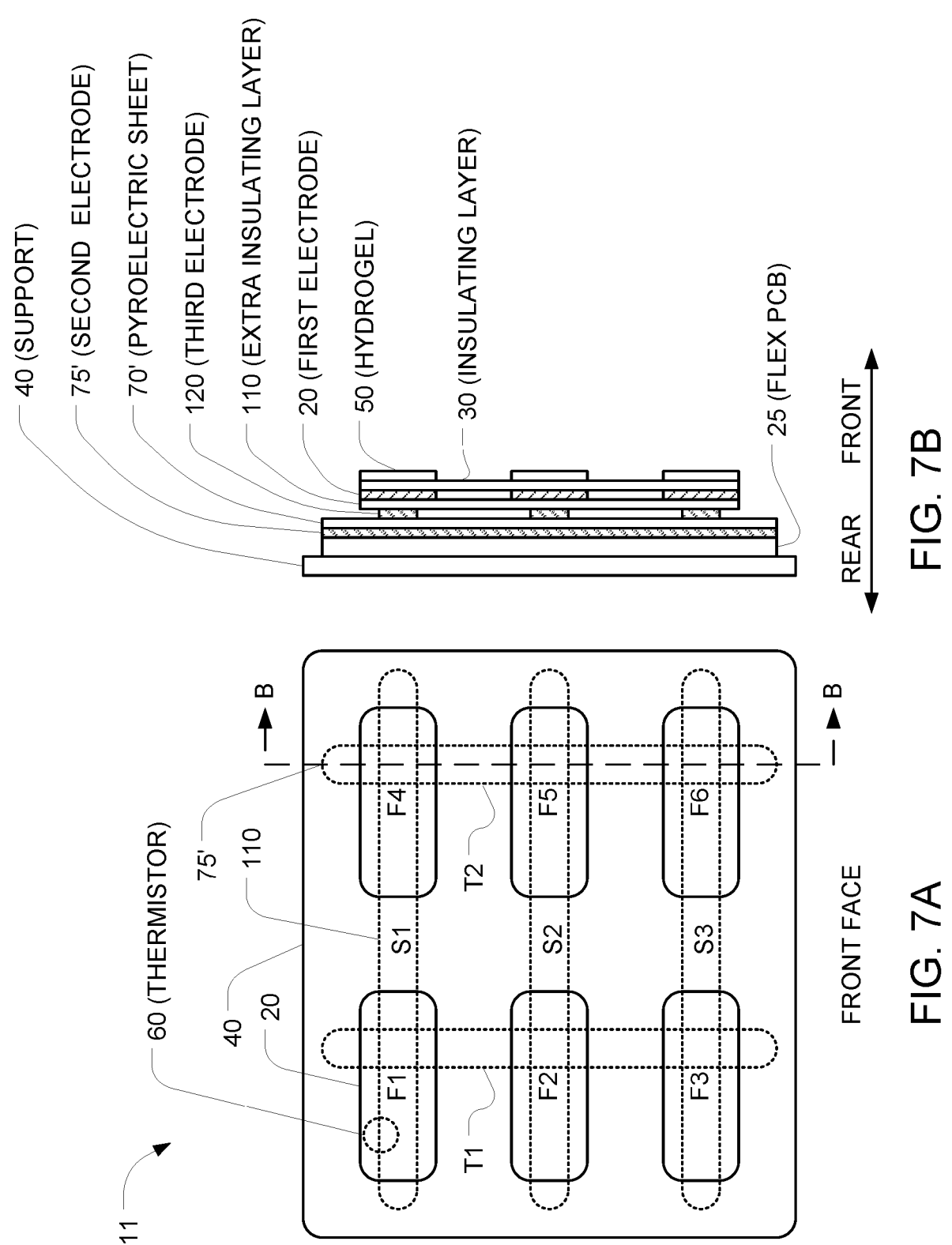
FIGS. 7A and 7B depict front and side views of an alternative approach for implementing a transducer array.

FIGS. 7A and 7B depict front and side views of an alternative approach for implementing a transducer array 11 which may be used in place of the transducer arrays 10L, 10R, 10A, and 10P depicted in FIG. 1. Optionally, this embodiment may be constructed using a flex circuit. The transducer array 11 is used for applying an electric field to a living subject, and it includes a plurality of first electrode elements 20. The first electrode elements are made from a conductive material (e.g., copper or another metal). Each of these first electrode elements 20 has a front face and a rear face. Note that although the example depicted in FIG. 7A/7B depicts only six first electrode elements 20 (labeled F1-F6) for simplicity, the actual number of first electrode elements 20 may vary from that value significantly (e.g., between 9 and 25, or between 4 and 50).

Similar to the FIG. 2A/2B embodiment described above, the transducer array 11 has a plurality of first conductive leads (not shown), and each of the first conductive leads is disposed in electrical contact with a respective one of the first electrode elements 20. These leads could be, for example, wires or traces on a PCB or flex circuit. And notably, because each of the first conductive leads corresponds to a respective one of the first electrode elements, it becomes possible to energize some of the electrode elements within any given transducer array without energizing all of the elements on that transducer array. This is accomplished by sending AC current into some (but not all) of the first conductive leads.

But unlike the FIG. 2A/2B embodiment described above, the first electrode elements 20 are not disposed in electrical contact with a region of pyroelectric material. Instead, an electrically insulating layer 110 is disposed on the rear face of each of the first electrode elements 20. The electrically insulating layer 110 is thermally conductive. A sheet of pyroelectric material 70' that has a rear face and a front face is positioned behind the electrically insulating layer 110 and disposed in thermal contact with the first electrode elements 20. The pyroelectric sheet 70' may be made from the same materials as the region 70 of pyroelectric material described above in connection with FIG. 2A/2B.

A plurality of second electrode regions 75' is positioned so that each of the second electrode regions 75' makes electrical contact with a respective region of the rear face of the pyroelectric sheet 70'. And a plurality of second conductive leads (not shown) is provided, each of which is disposed in electrical contact with a respective one of the second electrode regions 75'.

A plurality of third electrode regions 120 is positioned so that each of the third electrode regions 120 makes electrical contact with a respective region of the front face of the pyroelectric sheet 70', and these third electrode regions 120 are sandwiched between the pyroelectric sheet 70' and the electrically insulating layer 110. A plurality of third conductive leads (not shown) is provided, each of which is disposed in electrical contact with a respective one of the third electrode regions 120. The second electrode regions 75' and third electrode regions 120 are made from a suitable conductive material (e.g., copper or another metal).

In the embodiment depicted in FIG. 7A/7B, each of the second electrode regions 75' has a longitudinal axis that runs in the left-right direction on the page, and each of the third electrode regions 120 has a longitudinal axis that runs in the up-down direction on the page. As a result, the longitudinal axes of the second electrode regions 75' are perpendicular to the longitudinal axes of the third electrode regions 120. In alternative embodiments, these two axes are substantially perpendicular (i.e., offset by 80-100°). Note that in the illustrated embodiment, there are three horizontal second electrode regions 75', and two third electrode regions 120. But in alternative embodiments, the number of second electrode regions 75' can be anything greater than two (e.g., 4-25) and the number of third electrode regions 120 can be anything greater than two (e.g., 4-25).

Notably, because the second electrode regions 75' are substantially perpendicular to the third electrode regions 120, and the pyroelectric sheet 70' of pyroelectric material sits between the second electrodes and the third electrodes, signals that represent the change in temperature at any position where the second and third electrodes intersect can be obtained by selecting the corresponding second and third electrodes. For example, a signal that represents the change in temperature at the intersection between the second electrode element 75' S1 and third electrode element 120 T1 can be obtained by measuring an electrical signal that originates from the pyroelectric material at that location using those two electrode elements S1, T1. Similarly, a signal that represents the change in temperature at the intersection between the second electrode element 75' S3 and third electrode element 120 T2 can be obtained by measuring an electrical signal that originates from the pyroelectric material at that location using those two electrode elements S3, T2.

When the number of second and third electrode regions 75', 120 is relatively small (as depicted in FIG. 7A/7B), the perpendicular arrangement of the second and third electrode elements does not provide a significant reduction in the number of conductors that must be routed to the transducer array 11 in order to measure the change in temperature at all the intersections between the second and third electrode regions. But when the number of second and third electrode regions 75' and 120 becomes larger (e.g., each being greater than four), the perpendicular arrangement of the second and third electrode elements will significantly reduce the number of conductors that are needed to measure the change in temperature at all the intersections between the second and third electrode elements.

Each intersection between any given second electrode region 75' and a given third electrode region 120 can be used to measure the temperature change that occurs in the section of the pyroelectric sheet 70' positioned at that intersection. And because each section of the pyroelectric sheet 70' is disposed in thermal contact with a portion of the transducer array 11, the configuration depicted in FIG. 7A/7B can be used to measure the changes in temperature at various positions distributed throughout the transducer array 11. These measured changes in temperature can be used in the same way that the measured changes in temperature are used in the FIG. 2A/2B embodiment.

Optionally, one or more of a self-adhesive support structure 40, regions 30 of a dielectric material with a dielectric constant of at least 20, hydrogel 50, and at least one thermistor 60 may be included in this FIG. 7A/7B embodiment as described above in connection with the FIG. 2A/2B embodiment. Optionally, the areas of the plurality of first electrode elements collectively add up to at least 25 cm$^2$.

Figure 8:
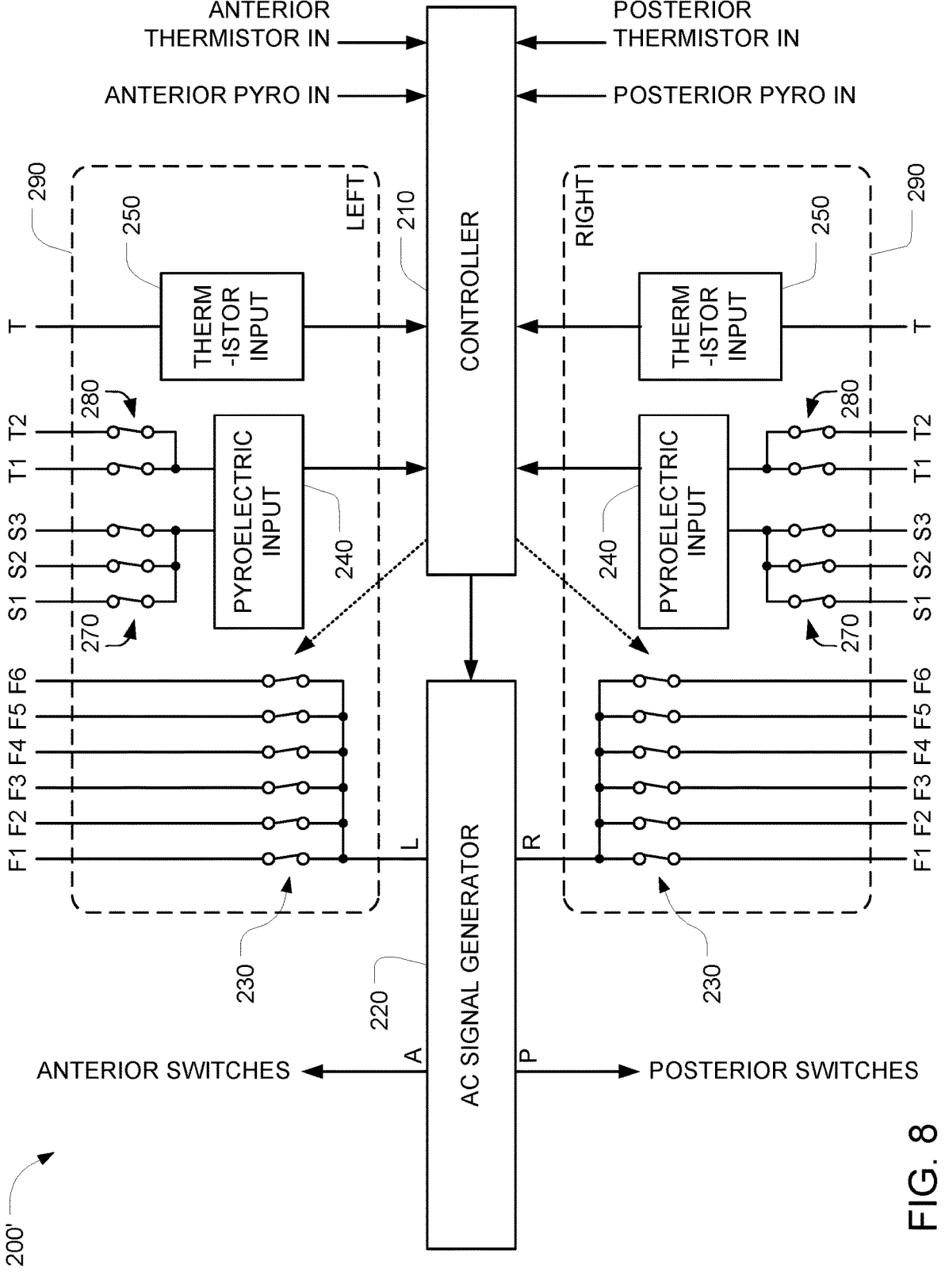
FIG. 8 depicts an embodiment of a TTFields system for interfacing with the transducer arrays depicted in FIG. 7A/7B.

FIG. 8 depicts an embodiment of a TTFields system 200' for interfacing with the transducer arrays 11 depicted in FIG. 7A/7B. Operation of this embodiment is the same as the FIG. 4 embodiment in all regards with the exception of the way the input signals are obtained from the pyroelectric regions and routed to the amplifier 240. More specifically, in the FIG. 4 embodiment, only a single bank of switches 260 was required to select a signal from any given region of pyroelectric material. But in view of the intersecting nature of the second electrode region 75' and the third electrode regions 120 as described above in connection with FIG. 7A/7P, a single horizontal second electrode region 75' and a single vertical third electrode region 120 must be selected in order to obtain electrical signals from a given portion of the pyroelectric sheet 70'.

Accordingly, one bank of switches 270 is used to select a single one of the second electrode region 75' by closing only a single switch in that bank 270, and another bank of switches 280 is used to select a single one of the third electrode regions 120 by closing only a single switch in that bank 280. The controller 210 determines which switches to open and which switches to close depending on the intersection at which the controller wants to measure the changes in temperature. For example, if the controller 210 wants to measure the changes in temperature at the portion of pyroelectric material 70' that lies between the second electrode region 75' S1 and the third electrode region 120 T1, the controller 210 sends a command to close only the switch on the left side of the switch bank 270 and to close only the switch on the left side of the bank 280. Similarly, if the controller 210 wants to measure the changes in temperature at the portion of pyroelectric material 70' that lies between the second electrode region 75' S2 and the third electrode region 120 T2, the controller 210 sends a command to close only the middle switch in the switch bank 270 and to close only the switch on the right side of the bank 280.

In the embodiments described above, the TTFields were switched every one second between the A/P channel and the L/R channel. But in alternative embodiments, the TTFields can be switched at a faster rate (e.g., every 100-1000 ms) or at a slower rate (e.g., every 1-5 seconds).

The overall duration of treatment is preferably at least 1 hour long, and is more preferably at least 100 or at least 1000 hours long. Optionally, the overall duration of treatment may be interrupted by breaks. For example, applying the alternating fields to a subject for 15 hours per day for 100 days (with a break from treatment each night while the subject sleeps) would result in a total duration of treatment of 1500 hours.

In the embodiments described above, the direction of the TTFields was switched between two perpendicular directions by applying an AC voltage to two pairs of electrodes (10A/10P and 10L/10R) that are disposed about 90° apart from each other in an alternating sequence. But in alternative embodiments the direction of the TTFields may be switched between two directions that are not perpendicular by repositioning the pairs of electrodes, or between three or more directions (assuming that additional pairs of electrodes are provided). For example, the direction of the TTFields may be switched between three directions, each of which is determined by the placement of its own pair of electrodes. In other alternative embodiments, the electrodes need not be arranged in pairs. See, for example, the electrode positioning described in U.S. Pat. No. 7,565,205, which is incorporated herein by reference. In other alternative embodiments, the direction of the field remains constant.

The methods described herein can be used to apply TTFields to a target region of a live subject's body, for both glioblastoma and other types of cancer. This may be accomplished, for example, by positioning electrodes on or below the subject's skin so that application of an AC voltage between selected subsets of those electrodes will impose the TTFields in the target region of the subject's body. For example, in situations where the relevant cells are located in the subject's lungs, one pair of electrodes could be positioned on the front and back of the subject's thorax, and a second pair of electrodes could be positioned on the right and left sides of the subject's thorax. By using the methods and apparatuses described herein, the growth of cancer cells or tumors can be inhibited.

Although the discussion above is presented in the context of applying TTFields to a target region of a subject's body for the purpose of treating a tumor, the same concepts can be used when applying alternating electric fields to a subject's body for other purposes, including but not limited to increasing the permeability of the blood brain barrier and increasing the permeability of cell membranes, as described in U.S. Pat. Nos. 10,967,167 and 11,103,698, each of which is incorporated herein by reference in its entirety.

Embodiments illustrated under any heading or in any portion of the disclosure may be combined with embodiments illustrated under the same or any other heading or other portion of the disclosure unless otherwise indicated herein or otherwise clearly contradicted by context.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. An apparatus for applying an electric field to a living subject, the apparatus comprising:
a plurality of first electrode elements, each of the first electrode elements having a front face and a rear face;
a plurality of first conductive leads, wherein each of the first conductive leads is disposed in electrical contact with a respective one of the first electrode elements;
a plurality of regions of a pyroelectric material, each of the regions of the pyroelectric material having a front face and a rear face, wherein the front face of each of the regions of the pyroelectric material is disposed in electrical and thermal contact with the rear face of the respective one of the first electrode elements;
a plurality of second electrode regions, each of which contacts the rear face of a respective one of the regions of the pyroelectric material;
at least one second conductive lead disposed in electrical contact with the plurality of second electrode regions; and
at least one temperature sensor positioned in thermal contact with at least one of the first electrode elements.

2. The apparatus of claim 1, wherein each of the second electrode regions is non-contiguous with all other second electrode regions, and wherein the at least one second conductive lead comprises a plurality of conductive leads, each of which is disposed in electrical contact with a respective one of the second electrode regions.

3. The apparatus of claim 1, wherein each of the second electrode regions is non-contiguous with all other second electrode regions, and wherein the at least one second conductive lead comprises a single lead disposed in electrical contact with all the second electrode regions.

4. The apparatus of claim 1, wherein all of the second electrode regions lie within a single sheet of conductive material, and wherein the at least one second conductive lead is disposed in electrical contact with the single sheet of conductive material.

5. The apparatus of claim 1, wherein each of the regions of the pyroelectric material is non-contiguous with all other regions of the pyroelectric material.

6. The apparatus of claim 1, wherein all of the regions of the pyroelectric material lie within a single sheet of pyroelectric material.

7. The apparatus of claim 1, wherein the at least one temperature sensor comprises at least one thermistor.

8. The apparatus of claim 1, further comprising:
a plurality of regions of a dielectric material with a dielectric constant of at least 20, wherein each of the regions of the dielectric material is disposed on the front face of a respective one of the first electrode elements, and
a self-adhesive support structure configured to hold the front face of each of the first electrode elements against a portion of the subject's body with the regions of the dielectric material disposed between the front face of the first electrode elements and the subject's body.

9. The apparatus of claim 8 further comprising a layer of hydrogel disposed between the regions of the dielectric material and the subject's body.

10. An apparatus for applying an electric field to a living subject, the apparatus comprising:
a plurality of first electrode elements, each of the first electrode elements having a front face and a rear face;

a plurality of first conductive leads, wherein each of the first conductive leads is disposed in electrical contact with a respective one of the first electrode elements;

an electrically insulating layer disposed on the rear face of each of the first electrode elements, wherein the electrically insulating layer is thermally conductive;

a sheet of pyroelectric material having a rear face and a front face, wherein the sheet of pyroelectric material is positioned behind the electrically insulating layer and disposed in thermal contact with the first electrode elements;

a plurality of second electrode regions positioned so that each of the second electrode regions makes electrical contact with a respective region of the rear face of the pyroelectric material;

a plurality of second conductive leads, each of which is disposed in electrical contact with a respective one of the second electrode regions;

a plurality of third electrode regions positioned so that each of the third electrode regions makes electrical contact with a respective region of the front face of the pyroelectric material, wherein the third electrode regions are sandwiched between the pyroelectric material and the electrically insulating layer; and a plurality of third conductive leads, each of which is disposed in electrical contact with a respective one of the third electrode regions.

11. The apparatus of claim 10, wherein each of the second electrode regions has a longitudinal axis, wherein each of the third electrode regions has a longitudinal axis, and wherein the longitudinal axes of the second electrode regions are substantially perpendicular to the longitudinal axes of the third electrode regions.

12. The apparatus of claim 10, further comprising:

a plurality of regions of a dielectric material with a dielectric constant of at least 20, wherein each of the regions of the dielectric material is disposed on the front face of a respective one of the first electrode elements, and a self-adhesive support structure configured to hold the front face of each of the first electrode elements against a portion of the subject's body with the regions of the dielectric material disposed between the front face of the first electrode elements and the subject's body.

13. The apparatus of claim 12 further comprising a layer of hydrogel disposed between the regions of the dielectric material and the subject's body.

14. The apparatus of claim 10, further comprising at least one thermistor positioned in thermal contact with at least one of the first electrode elements.

* * * * *